United States Patent [19]

Gross et al.

[11] Patent Number: 5,062,834

[45] Date of Patent: Nov. 5, 1991

[54] DEVICE FOR DISPENSING A LIQUID PARTICULARLY USEFUL FOR DELIVERING MEDICAMENTS AT A PREDETERMINED RATE

[75] Inventors: Joseph Gross, Moshav Mazor; Shlomo Zucker, Yavne, both of Israel

[73] Assignee: Product Development (S.G.Z.) Ltd, Petah Tikua, Israel

[21] Appl. No.: 393,739

[22] Filed: Aug. 15, 1989

[30] Foreign Application Priority Data

Feb. 24, 1989 [IL] Israel .......................................... 89400
Jun. 30, 1989 [IL] Israel .......................................... 90816

[51] Int. Cl.⁵ .............................................. A61M 37/00
[52] U.S. Cl. ..................................... 604/143; 604/145
[58] Field of Search ............... 604/143, 145, 151, 144; 222/386, 386.5, 389

[56] References Cited

U.S. PATENT DOCUMENTS

| | | | |
|---|---|---|---|
| 3,022,785 | 10/1962 | Crockford et al. | 604/145 |
| 3,115,280 | 12/1963 | Battista | 222/95 |
| 3,308,818 | 3/1967 | Rutkowski | 222/386.5 X |
| 3,433,224 | 3/1969 | Black | 604/143 |
| 3,468,308 | 9/1969 | Bierman | 128/214 |
| 3,640,277 | 2/1972 | Adleberg . | |
| 3,871,553 | 3/1975 | Steinberg | 222/95 |
| 4,351,335 | 9/1982 | Whitney et al. | 604/143 |
| 4,561,856 | 12/1985 | Cochran | 604/143 |
| 4,662,872 | 5/1987 | Cane | 604/151 |
| 4,744,786 | 5/1988 | Hooven | 604/143 |

FOREIGN PATENT DOCUMENTS

| | | |
|---|---|---|
| 0209644 | 1/1987 | European Pat. Off. . |
| 2195461 | 8/1974 | France . |
| 8800065 | 1/1988 | PCT Int'l Appl. . |

Primary Examiner—Richard J. Apley
Assistant Examiner—L. Thomas
Attorney, Agent, or Firm—Benjamin J. Barish

[57] ABSTRACT

A device for dispensing a liquid, particularly a medicament, at a predetermined rate, includes a container including a displaceable partition to define a first expansible-contractible chamber on one side for receiving the liquid to be dispensed, and a second expansible-contractible chamber on the opposite side for receiving an electrolytic cell. The electrolytic cell has electrodes and an electrolyte capable of generating, upon the energization of the electrodes, a gas under pressure to thereby displace the displaceable partition and to force the liquid out from the first chamber in accordance with the rate of energization of the electrodes. The displaceable partition includes a piston assembly having a pair of pistons spaced apart by a connecting stem, the container being formed with a vent opening in the space between the pistons to prevent accidental mixing of the gas with the liquid to be dispensed.

8 Claims, 3 Drawing Sheets

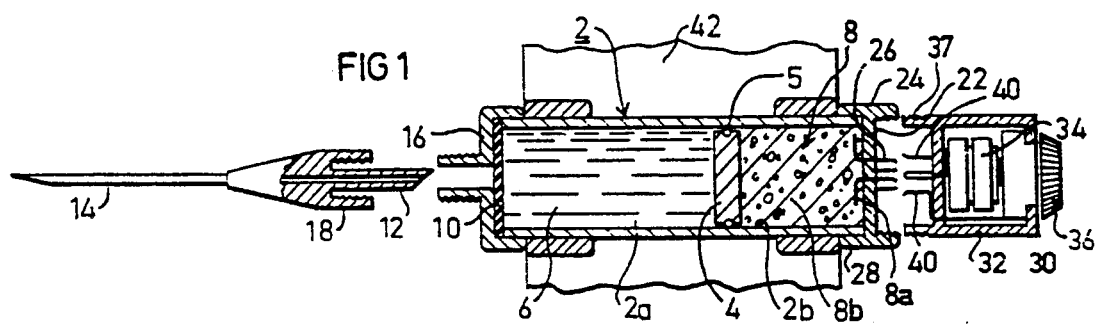
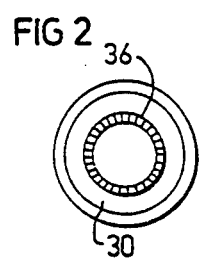
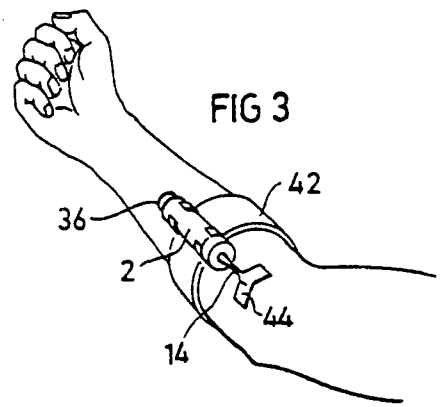
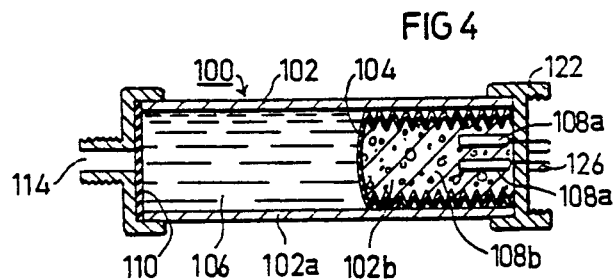

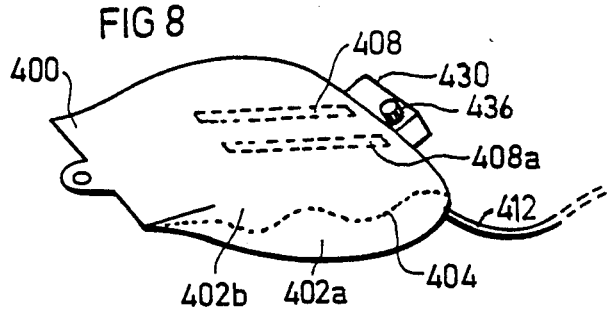
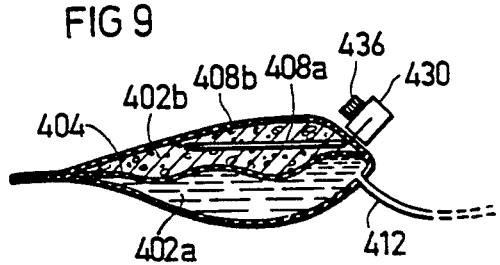
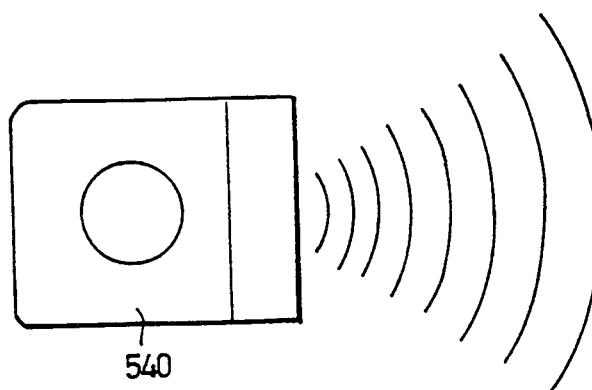
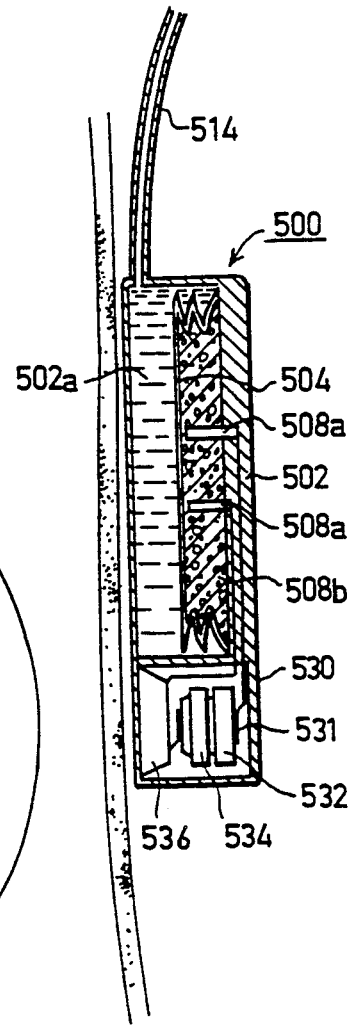

DEVICE FOR DISPENSING A LIQUID PARTICULARLY USEFUL FOR DELIVERING MEDICAMENTS AT A PREDETERMINED RATE

BACKGROUND OF THE INVENTION

The present invention relates to a device for dispensing a liquid. The invention is particularly useful for delivering medicaments at predetermined rates, and is therefore described below, with respect to this application.

There are many applications requiring the dispensing or delivering of a liquid at predetermined or precisely controlled rates. One of the applications requiring particularly precise rates of delivery are systems for administering insulin or other medicaments, and very precise pumps have been devised for this purpose. However, such pumps are expensive to produce and maintain, and are inconvenient to refill with the periodic dosage requirements.

It has been proposed, particularly in such applications, to use as the liquid dispensing device a container for receiving a supply of the liquid to be dispensed, and an arrangement for subjecting the liquid to a pressurized gas to force the liquid from the container. Examples of such known systems are illustrated in U.S. Pat. No. 3,640,277 disclosing a gas cartridge for supplying the gas pressure, U.S. Pat. No. 3,468,308 disclosing an inflated bladder for supplying the gas pressure, and U.S. Pat. No. 3,871,553 connectable to a compressed air hose for supplying the air pressure. All such known arrangements, however, require a valve which must be precisely controlled in order to control the rate of delivery of the liquid to be dispensed. Such precise control is extremely difficult when very low rates of delivery are required as in the case of delivery of insulin or other types of medicaments.

OBJECTS AND SUMMARY OF THE PRESENT INVENTION

An object of the present invention is to provide a device for dispensing a liquid, at precisely controllable rates. Another object of the invention is to provide a device particularly useful for delivering medicaments at predetermined rates. A further object is to provide to a device which includes a few simple parts producible in volume and at low cost, and thereby practicable to be incorporated in disposable devices for one-time use.

According to the present invention, there is provided a device for dispensing a liquid at a predetermined rate, comprising a container for receiving a supply of the liquid to be dispensed, and means for subjecting the liquid to a pressurized gas to force liquid from the container. The device includes a piston assembly movable within the container and dividing it into a first expansible-contractible chamber for receiving the liquid to be dispensed, and a second expansible-contractible chamber for receiving the pressurized gas to dispense liquid from the first chamber of the container. The piston assembly includes a pair of pistons spaced apart by a connecting stem, and the container is formed with a vent opening in the space between the pistons to provide protection against inadvertent mixing of the gas from the second chamber with the liquid in the first chamber.

Several embodiments of the invention are described below for purposes of example.

According to further features in all the described embodiments, the second expansible-contractible chamber includes an electrolytic cell having electrodes adapted to be electrically energized, and an electrolyte capable of generating the gas upon the energization of the electrodes, to thereby dispense the liquid from the container in accordance with the rate of energization of the electrodes.

A further embodiment is described wherein the common container is a pliable bag, and the displaceable partition member is a flexible diaphragm dividing the interior of the bag into the first and second chambers. Such a construction is particularly useful as an infusion device for producing the required pressure to be applied to the infusion liquid (e.g., saline water, blood plasma, etc.) when it is not possible or convenient to suspend the infusion bag above the patient, or when it is desired or necessary to provide a higher rate of infusion than that produced by suspending the infusion bag above the patient.

A still further embodiment of the invention is described wherein the container is implantable in a human being or animal, and the device includes an electrical power supply having a control circuit including an electrical relay controlled by a remotely-located transmitter for controlling the energization of the electrodes, and thereby the rate of dispensing the liquid from the first chamber.

Further features and advantages of the invention will be apparent from the description below.

BRIEF DESCRIPTION OF THE DRAWINGS

The invention is herein described, by way of example only, with reference to the accompanying drawings, wherein:

FIG. 1 is an exploded longitudinal sectional view illustrating one form of liquid dispensing device constructed in accordance with the present invention;

FIG. 2 is an end elevational view of the device of FIG. 1;

FIG. 3 illustrates one manner of using the liquid dispensing device of FIGS. 1 and 2 for administering a medicament, such as insulin, in a controlled manner over a period of time;

FIGS. 4–6 illustrate three further forms of liquid dispensing devices constructed in accordance with the invention;

FIGS. 8 and 9 are sectional and three-dimensional views, respectively, illustrating a further form of liquid-dispensing device constructed in accordance with the invention and particularly useful with infusion bags; and FIG. 10 is a longitudinal sectional view illustrating the invention embodied in a device implantable in a human being or animal and controlled by a remotely located transmitter.

DESCRIPTION OF PREFERRED EMBODIMENTS

THE EMBODIMENT OF FIGS. 1–3

Figure 5:
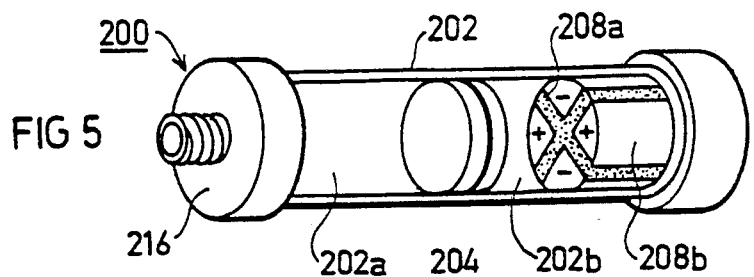

The device illustrated in FIGS. 1–3 includes a container 2 whose interior is divided into two chambers 2a, 2b by a displaceable partition member in the form of a piston 4 including a sealing ring 5. Chamber 2a is adapted to contain the liquid 6, e.g., a medicament (such as insulin) to be dispensed, and chamber 2b is adapted to contain an electrolytic cell, generally designated 8, comprising a pair of electrodes 8a and an electrolyte 8b capable of generating, upon the energization of the electrodes, a gas which expands chamber 2b, displaces piston 4, and thereby forces the liquid 6 out from chamber 2a in accordance with the rate of energization of the electrodes.

In the device illustrated in FIG. 1, the discharge end of chamber 2a is closed by a membrane 10 pierceable by the pointed end 12 of a syringe needle 14 when attached to a fitting 16 closing the respective end of the container adjacent membrane 10. Thus, as shown in FIG. 1, fitting 16 is formed with external threads, to receive an internally-threaded collar 18 formed in the syringe needle 14. When the syringe needle is thus applied to fitting 16, the pointed end 12 of the needle pierces membrane 10 to thereby enable the contents 6 of chamber 2a to be discharged via a bore formed in the syringe needle 14.

As shown in FIG. 1, the electrodes 8a of the electrolytic cell 8 within chamber 2b include electrical conductors passing through an end wall 22 formed in a fitting 24 closing the respective end of container 2 and terminate in connector terminals 26 externally of the container. Fitting 24 is formed with an internally threaded collar 28 adapted to receive a housing unit 30 containing the power supply and controls for controlling the energization of electrodes 8a, and thereby for controlling the rate of dispensing of the contents 6 of chamber 2a via syringe needle 14. Thus, housing 30 includes a battery 32, and a control circuit 34 controlled by an external knob 36, which knob may also include an on/off switch. The power supply and control unit 30 is provided with a collar 37 externally threaded so as to be attachable to collar 28 of the container unit 6. Unit 30 further includes connector terminals 40 adapted to engage connector terminals 26 of container unit 6 when attached thereto.

Container unit 2 may be fixed to a band or strap 42 for attachment to the body, e.g., the arm, of the person to receive the medicament dispensed from chamber 2a of the container 6 via the syringe needle 14. As shown in FIG. 3, the syringe needle 14 is passed through the recipient's skin into a vein, and is immobilized therein by an adhesive strip 44. The container 2, including the power-supply unit 30 attached thereto, is fixed to the recipient's arm by band 42. Knob 36 may be rotated to supply current from the battery 32 within unit 30, via connector terminals 40 and 26, to the electrodes 8a within the electrolytic-cell compartment 2b of the container, to cause the electrolyte 8b within that container to generate a gas. The generated gas produces a force moving piston 4 (leftwardly in FIG. 1), which thereby causes the medicament 6 within chamber 2a to be forced out of the hole formed through membrane 10 when the syringe needle 14 was attached, and to be administered to the recipient via syringe needle 14.

The electrolyte 8b of the electrolytic cell 8 within compartment 2b may be any appropriate material, preferably of liquid of gel form, which generates a gas upon the energization of the electrodes 8a and in accordance with the rate of energization of the electrodes. Control circuit 34, controlled by knob 36, may include an on/off switch which starts the energization of the electrodes, and a potentiometer which controls the rate of energization, thereby enabling the rate of administering the medicament 6 within chamber 2a to be controlled by knob 36.

Examples of the electrolyte 8b which may be used include saline solution, other polar solutions or gels, generating hydrogen, oxygen, nitrogen or carbon dioxide.

THE EMBODIMENT OF FIG. 4

The device illustrated in FIG. 4, and therein generally designated 100, is similar to that illustrated in FIGS. 1 and 2 in that it includes a container 102 whose interior is divided into the two chambers 102a, 102b by a displaceable partition member 104. In this case, however, the displaceable partition member 104 is in the form of a flexible diaphragm, rather than in the form of a piston. Diaphragm 104 is preferably a rolling diaphragm permitting a high degree of expansion upon the generation of a gas from the electrolyte 108b within chamber 102b in order to contract chamber 102a, and thereby to force out the liquid, e.g., a medicament, from that chamber.

In all other respects, the device illustrated in FIG. 4 is constructed and operates in the same manner as the device illustrated in FIGS. 1-3, Thus, the FIG. 4 device also includes a membrane 110 closing the end of the medicament-containing chamber 102a and pierceable by a syringe needle, when attached to fitting 114, for dispensing the medicament through the syringe needle. The electrolytic cell chamber 102b includes not only the electrolyte 108b (which may be a liquid or a gel), but also the pair of electrodes 108a at the opposite end of container 102 connected to terminals 126 in end wall 122 and adapted to be energized by the power supply unit (30 in FIG. 1, not shown in FIG. 4). As described above, the rate of energization of the electrodes 108a controls the rate of generation of gasses from the electrolyte 108b, and thereby the rate of dispensing the liquid 106 from chamber 102a via the syringe needle to be attached to fitting 116 which pierces membrane 110.

THE EMBODIMENT OF FIG. 5

FIG. 5 illustrates a medicament delivery device, generally designated 200, also similar to that described in FIGS. 1 and 2, in that it includes a container 202 having a displaceable piston 204 dividing the interior of the container into a first chamber 202a for receiving the medicament to be delivered, and a second chamber 202b for receiving the electrolyte and electrodes of the electrolytic cell. In the embodiment of FIG. 5, however, the electrolyte 208a within chamber 202b is in the form of a gel disposed between sector-shaped electrodes 208b. When the electrodes 208a are energized, the gel produces a gas which is released in chamber 202b, thereby increasing the pressure applied to piston 204, which contracts chamber 202a to dispense the medicament therein via fitting 216 and the syringe needle (not shown) attached to that filling.

THE EMBODIMENTS OF FIGS. 6 AND 7

Figure 6:
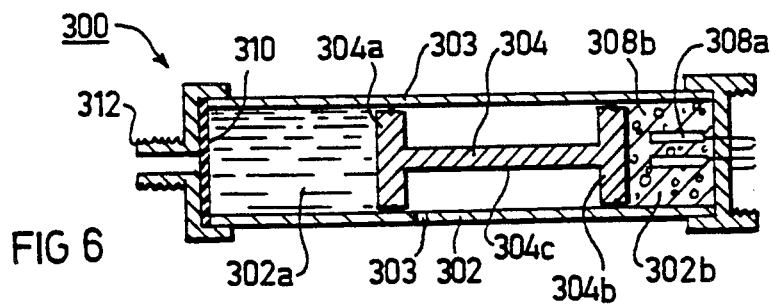

FIG. 6 illustrates a medicament delivery device, generally designated 300, which is similar to FIG. 5, it includes a piston assembly 304 serving as the displaceable partition member within the container 302 dividing it into the drug-receiving chamber 302a and the electrolytic cell chamber 302b. In FIG. 6, however, piston 304 is an assembly which includes two pistons 304a and 304b spaced apart by an axially extending stem 304c joining the two pistons. In addition, container 302 is formed with vent openings 303 in the space between the two pistons 304a, 304b. This construction isolates the drug in chamber 302a from the electrolyte 308b in chamber 302b, and also from the gas generated within that chamber by the energization of the electrodes 308a, since such electrolyte or gas, if it does penetrate past piston 304b, will be vented to the atmosphere via vent openings 302a. The end of the drug-receiving chamber 302a is also closed by a membrane 310 pierceable by a syringe needle when attached to fitting 312.

Figure 7:
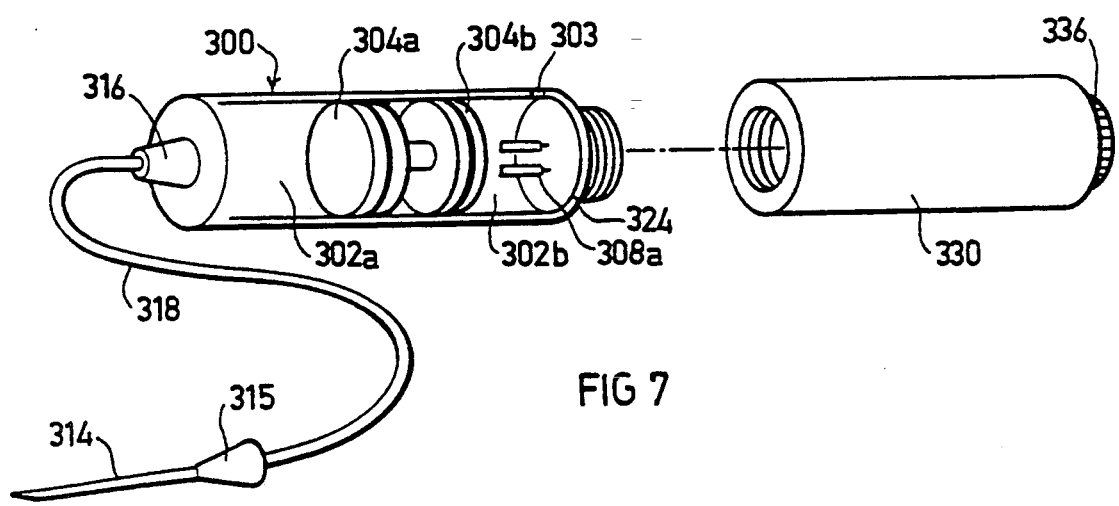
FIG. 7 is a three-dimensional view of the embodiment of FIG. 6.

FIG. 7 illustrates a complete medicament delivery device utilizing the double-piston construction of FIG. 6. Thus, the syringe needle 314, including its fitting 315, is adapted to be attached to fitting 316 closing the end of the drug-receiving chamber 302a. In this case, however, the syringe needle 314 is connected to fitting 316 via another flexible tube 318, the latter tube including a piercing element for piercing the membrane (10, FIG. 1) to permit the delivery of the drug from chamber 302a to the syringe needle 314.

FIG. 7 also illustrates the power supply unit 330 attachable to the fitting 324 at the opposite end of container 302 for energizing the electrodes within the electrolytic cell compartment 302b which generate the propelling gas. As in the other described embodiments, the power supply unit 330 includes the battery for energizing the electrodes 308a, the control circuit for controlling the energization of the electrodes, and the presetting knob 336 for presetting the rate of energization of the electrodes, and thereby the rate of delivery of the drug from compartment 302a.

THE EMBODIMENTS OF FIGS. 8 AND 9

FIGS. 8 and 9 illustrate another liquid-delivery device, generally designated 400, for delivering an infusion liquid from an infusion bag. In this case, the container is a pliable plastic bag 402, and the displaceable partition member is a flexible diaphragm 404 dividing the interior of the bag into the liquid-containing compartment 402a and the electrolytic cell compartment 402b. The electrolyte 408b within compartment 402b is preferably a gel, and the electrodes 408a are preferably in the form of two relatively-long rods extending for a substantial part of the length of chamber 402b. The electrodes are energized by a power supply unit 430 connected to the electrodes 408b. Power supply unit 430 includes, in addition to the battery, an electrical switch and a control circuit (e.g., a rheostat) both controlled by rotary knob 436. As described above, knob 436 thus initiates the energization of the electrodes 408b, and also controls the rate of energization of the electrodes, and thereby the rate of dispensing the liquid from chamber 402a via its outlet tube 412 to the patient.

The infusion bag construction illustrated in FIGS. 8 and 9 may be used for infusion of saline water, blood plasma, intravenous feeding, etc. Since it generates its own pressure, it obviates the need for hanging the infusion bag over the patient where this may be difficult or inconvenient. In addition, it can be controlled to preselect the rate of feeding of the infusion liquid, particularly where it may be desired to have a higher infusion rate than possible by using the pressure head of a suspended infusion bag.

THE EMBODIMENT OF FIG. 10

FIG. 10 illustrates a drug delivery system, generally designated 500, designed to be implanted in a human or animal. The device includes a container 502 whose interior is divided by a rolling diaphragm 504 into a drug-containing chamber 502a and an electrolytic cell chamber 502b. The latter chamber includes an electrolyte 508b, preferably of the gel type, immersing a pair of electrodes 508a. The electrodes are supplied by a power supply unit 530 also implanted with the container 502. The power supply unit 530 includes a connector terminal 531 engageable with the terminal of a battery 532, an electrical control circuit 534, and an electrical switch 536 controlling the energization of the electrodes 508b, which generate a gas and force the contents of chamber 102a out through feed tube 514 at a rate controlled by the energization of the electrodes.

Electrical switch 536 may be operated at the time the device is implanted, or may be operated subsequently to that time by a remotely-located transmitter, as shown at 540. In the latter case, the control circuit 534 within the implanted power supply 530 would also include an electrical relay (preferably electronic switch) controlled by the remotely-located transmitter 540.

It will be appreciated that in all the above-described embodiments, the rate of energization of the electrodes may be controlled to dispense the liquid at a constant preselected rate, or at different rates, e.g., according to different times of the day. Such variable controls are well-known in drug-delivery systems wherein the control circuit is in the form of a microprocessor which may be pre-programmed to deliver the drug at different rates.

While the invention has been described with respect to several preferred embodiments, it will be appreciated that many other variations, modifications and applications of the invention may be made.

What is claimed is:

1. A device for dispensing a liquid at a predetermined rate, comprising a container for receiving a supply of the liquid to be dispenses, and means for subjecting the liquid to a pressurized gas to force liquid from the container; characterized in that said device includes a piston assembly movable within said container and dividing same into a first expansible-contractible chamber for receiving the liquid to be dispenses, and a second expansible-contractible chamber for receiving the pressurized gas to dispense liquid from said first chamber of the container; said piston assembly comprising a pair of pistons spaced apart by a connecting stem; said container being formed with a vent opening in the space between said pistons to provide protection against inadvertent mixing of the gas from the second chamber with the liquid in the first chamber.

2. The device according to claim 1, wherein said second expansible-contractible chamber includes an electrolytic cell having electrodes adapted to be electrically energized, and an electrolyte capable of generating, upon the energization of the electrodes, the gas to thereby dispense the liquid from the container in accordance with the rate of energization of said electrodes.

3. The device according to claim 2, wherein the end of said container through which the liquid is to be dispensed is closed by a membrane pierceable by a needle to permit dispensing the liquid.

4. The device according to claim 2, further including an electrical power supply for energizing said electrodes, said electrical power supply being housed within a separate power supply unit attachable to said container.

5. The device according to claim 4, wherein said power supply unit includes a battery and an electrical control circuit for controlling the rate of energization of the electrode, and thereby the rate of dispensing the liquid from the container.

6. The device according to claim 5, wherein said electrical control circuit includes presettable means for presetting the rate of energization of the electrodes, and an electrical switch for controlling the energization of the electrodes.

7. A device for dispensing a liquid, particularly useful for delivering a medicament at a predetermined rate, comprising:
- a container including a displaceable partition to define a first expansible-contractible chamber on one side thereof for receiving the liquid to be dispenses, and a second expansible-contractible chamber on the opposite side thereof;
- and an electrolytic cell disposed in said second chamber;
- said electrolytic cell having electrodes adapted to be electrically energized, and an electrolyte capable of generating, upon the energization of the electrodes, a gas under pressure to thereby displace said displaceable partition and to force the liquid out from the first chamber in accordance with the rate of energization of said electrodes;
- said displaceable partition comprising a pair of pistons spaced apart by a connecting stem, said container being formed with a vent opening in the space between said pistons.

8. The device according to claim 7, wherein said container is a pliable bag, and said displaceable partition member is a flexible diaphragm dividing the interior of the pliable bag into said first and second chambers.

* * * * *